US008188003B2

(12) United States Patent
Köhle et al.

(10) Patent No.: US 8,188,003 B2
(45) Date of Patent: May 29, 2012

(54) METHOD OF INDUCING VIRUS TOLERANCE OF PLANTS

(75) Inventors: Harald Köhle, Bobenheim (DE); Uwe Conrath, La Calamine (BE); Kai Seehaus, Wiesbaden (DE); Matthias Niedenbrück, Limburgerhof (DE); Marco-Antonio Tavares-Rodrigues, Sao Paulo (BR); Waldemar Sanchez, Sao Bernardo do Campo (BR); Edson Begliomini, Sao Paulo (BR); Claudio Oliveira, Sao Bernardo do Campo (BR)

(73) Assignee: BASF Aktiengesellschaft, Ludwigshafen (DE)

( * ) Notice: Subject to any disclaimer, the term of this patent is extended or adjusted under 35 U.S.C. 154(b) by 383 days.

(21) Appl. No.: 11/230,454

(22) Filed: Sep. 21, 2005

(65) Prior Publication Data

US 2006/0172887 A1 Aug. 3, 2006

(51) Int. Cl.
*A01N 25/00* (2006.01)

(52) U.S. Cl. ...................... 504/116.1; 504/320; 504/321

(58) Field of Classification Search .................. 514/116, 514/116.1, 320, 321
See application file for complete search history.

(56) References Cited

U.S. PATENT DOCUMENTS

| | | | | | |
|---|---|---|---|---|---|
| 5,229,384 | A | | 7/1993 | Kunz et al. | |
| 5,824,705 | A | * | 10/1998 | Mueller et al. | 514/485 |
| 5,866,599 | A | * | 2/1999 | Schelberger et al. | 514/352 |
| 5,889,059 | A | * | 3/1999 | Bayer et al. | 514/619 |
| 5,945,380 | A | | 8/1999 | Gallenkamp et al. | |
| 5,981,532 | A | * | 11/1999 | Mueller et al. | 514/256 |
| 6,028,093 | A | * | 2/2000 | Muller et al. | 514/384 |

FOREIGN PATENT DOCUMENTS

| | | |
|---|---|---|
| GB | 2 224 209 A | 5/1990 |
| WO | WO 96/01256 | 1/1996 |
| WO | WO 98/29537 | 7/1998 |

OTHER PUBLICATIONS

Gullino, L., Uses and challenges of novel compounds for plant disease control, Elsevier, Crop Protection 19 (2000), p. 1-11.*

MSU Cares, URL<http://msucares.com/lawn/tree_diseases/repeat.html>.*

Pernezny, K., Disease Control for Florida Tomatoes, URL<http://edis.ifas.ufl.edu/VH056>.*

Hill et al., Endophyte Viability in Seedling Tall Fescue Treated with Fungicides, Crop Sci. 40:1490-1491 (2000).*

Ward, J.M., Frequency and Timing of Fungicide Applications for the Control of Gray Leaf Spot in Maize, The American Phytopathological Society, Plant Disease, Jan. 1997, pp. 41-48.*

MSU Cares, URL <http://msucares.com/lawn/tree_diseases/repeat.html>, 2001.*

Pernezny, K., Disease Control for Florida Tomatoes, URL<http://edis.ifas.ufl.edu/VH056>, 2000.*

* cited by examiner

*Primary Examiner* — Fereydoun G Sajjadi
*Assistant Examiner* — Danielle Sullivan
(74) *Attorney, Agent, or Firm* — Novak Druce + Quigg LLP

(57) ABSTRACT

A method of inducing virus tolerance of plants which comprises treating the plants, the soil or seeds with an effective amount of a compound of the formula I.

I

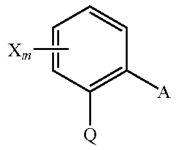

22 Claims, No Drawings

METHOD OF INDUCING VIRUS TOLERANCE OF PLANTS

The present invention relates to a method of inducing virus tolerance of plants which comprises treating the plants, the soil or seeds with an effective amount of a compound of the formula I

I

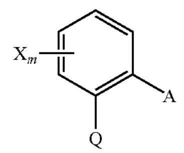

in which

X is halogen, $C_1$-$C_4$-alkyl or trifluoromethyl;

m is 0 or 1;

Q is C(═CH—$CH_3$)—$COOCH_3$, C(═CH—$OCH_3$)—$COOCH_3$, C(═N—$OCH_3$)—$CONHCH_3$, C(═N—$OCH_3$)—$COOCH_3$, N(—$OCH_3$)—$COOCH_3$, or a group Q1

Q1

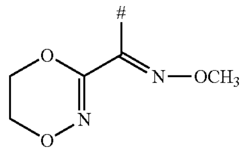

wherein # denotes the bond to the phenyl ring;

A is —O—B, —$CH_2$O—B, —O$CH_2$—B, —$CH_2$S—B, —CH═CH—B, —C≡C—B, —$CH_2$O—N═C($R^1$)—B, —$CH_2$S—N═C($R^1$)—B, —$CH_2$O—N═C($R^1$)—CH═CH—B, or —$CH_2$O—N═C($R^1$)—C($R^2$)═N—$R^3$, where B is phenyl, naphthyl, 5- or 6-membered hetaryl 5- or 6-membered hetero-cyclyl, containing one to three N atoms and/or one O or S atom or one or two O and/or S atoms, the ring systems being unsubstituted or substituted by one to three radicals $R^a$:

$R^a$ is cyano, nitro, amino, aminocarbonyl, aminothiocarbonyl, halogen, $C_1$-$C_6$-alkyl, $C_1$-$C_6$-haloalkyl, $C_1$-$C_6$-alkylcarbonyl, $C_1$-$C_6$-alkylsulfonyl, $C_1$-$C_6$-alkylsulfinyl, $C_3$-$C_6$-cycloalkyl, $C_1$-$C_6$-alkoxy, $C_1$-$C_6$-haloalkoxy, $C_1$-$C_6$-alkyloxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylamino-carbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, phenyl, phenoxy, benzyl, benzyloxy, 5- or 6-membered heterocyclyl, 5- or 6-membered hetaryl, 5- or 6-membered hetaryloxy, C(═NO$R^a$)—$R^b$ or OC($R^B$)$_2$—C($R^b$)═NO$R^b$, the cyclic radicals, in turn, being unsubstituted or substituted by one to three radicals $R^b$:

$R^b$ is cyano, nitro, halogen, amino, aminocarbonyl, aminothiocarbonyl, $C_1$-$C_6$-alkyl, $C_1$-$C_6$-haloalkyl, $C_1$-$C_6$-alkylsulfonyl, $C_1$-$C_6$-alkylsulfinyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylamino-carbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or C(═NO$R^A$)—$R^B$;

$R^A$, $R^B$ are hydrogen or $C_1$-$C_6$-alkyl;

$R^1$ is hydrogen, cyano, $C_1$-$C_4$-alkyl, $C_1$-$C_4$-haloalkyl, $C_3$-$C_6$-cycloalkyl, $C_1$-$C_4$-alkoxy, or $C_1$-$C_4$-alkylthio;

$R^2$ is phenyl, phenylcarbonyl, phenylsulfonyl, 5- or 6-membered hetaryl, 5- or 6-membered hetarylcarbonyl or 5- or 6-membered hetarylsulfonyl, the ring systems being unsubstituted or substituted by one to three radicals $R^a$, $C_1$-$C_{10}$-alkyl, $C_3$-$C_6$-cycloalkyl, $C_2$-$C_{10}$-alkenyl, $C_2$-$C_{10}$-alkynyl, $C_1$-$C_{10}$-alkylcarbonyl, $C_2$-$C_{10}$-alkenylcarbonyl, $C_3$-$C_{10}$-alkenylcarbonyl, $C_1$-$C_{10}$-alkylsulfonyl, or C(═NO$R^A$)—$R^B$, the hydrocarbon radicals of these groups being unsubstituted or substituted by one to three radicals $R^c$:

$R^c$ is cyano, nitro, amino, aminocarbonyl, aminothiocarbonyl, halogen, $C_1$-$C_6$-alkyl, $C_1$-$C_6$-haloalkyl, $C_1$-$C_6$-alkylsulfonyl, $C_1$-$C_6$-alkylsulfinyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkyloxy, 5- or 6-membered heterocyclyl, 5- or 6-membered heterocyclyloxy, benzyl, benzyloxy, phenyl, phenoxy, phenylthio, 5- or 6-membered hetaryl, 5- or 6-membered hetaryloxy and hetarylthio, it being possible for the cyclic groups, in turn, to be partially or fully halogenated or to have attached to them one to three radicals $R^a$; and $R^3$ is hydrogen, $C_1$-$C_6$-alkyl, $C_2$-$C_6$-alkenyl. $C_2$-$C_6$-alkynyl, the hydrocarbon radicals of these groups being unsubstituted or substituted by one to three radicals $R^c$;

which is taken up by the plants or seeds, during the first six weeks of the growth period of the plants or germination of the seeds.

A large number of representatives of the highly heterogeneous group of plant viruses (phytophages) are capable of attacking economically relevant plants; the symptoms of the damage range from morphological modifications to the death of the plants. The very many ways in which viruses are transmitted (for example mechanically via wounding, via seeds and pollen, or via vectors such as nematodes and insects), the problems of diagnosis and the lack of suitable active ingredients make the control of such viruses extraordinarily difficult; the emphasis is therefore on preventative and phytosanitary measures. Accordingly, preventing viral diseases in plants is an important aim in agriculture.

The search for methods for preventing viral diseases in plants has already yielded anti-viral active ingredients, some of which resemble nucleic acids. However, some of these substances generate mutants and inhibit the metabolism of nucleic adds and proteins in the host cells, giving rise to damage. In the field, these materials have only a small actual control effect.

A sophisticated principle is the utilization, or stimulation, of the plants' intrinsic defenses:

DE-A 39 34 761 proposes polylysine and alkyldiethylenetriaminoacetic acids for preventing viral diseases of plants. EP-A 420 803 describes the immunizing effect of benzo-1,2,3-thiazole derivatives against various phytopathogenic microorganisms. WO-A 96/37493 discloses a similar effect of pyridylthiazoles.

DD 280 030 proposes sulfonic acid derivatives as agents for activating the resistance of crop plants and useful plants. However, the action of these substances is unsatisfactory in many cases.

It is an object of the present invention to provide a method which can be used broadly, which does not damage the plants and which brings about effective immunization of the plants against viral diseases.

We have found that this object is achieved by the method defined at the outset. The active ingredients used are known as fungicides and, in some cases, also as insecticides (EP-A 178 826; EP-A 253 213; WO 93/15046; WO 95/18789; WO 95/21153; WO 95/21154; WO 95/24396; WO 96/01256; WO 97/15552; WO 97/27189). However, there has been no suggestion to date that these active ingredients might have a stimulatory effect on the plants' intrinsic immune system against viruses.

The good compatibility, with plants, of the active ingredients of the formula I at the concentrations required for controlling plant diseases permits the treatment of aerial plant parts and also the treatment of propagation material and seed, and of the soil.

In the method according to the invention, the active ingredients are taken up by the plant either through the roots, finally causing overall protection of the plant.

Thus, the protective action after carrying out the method according to the invention is not just found in those plant parts, which have been sprayed directly, but the tolerance to viral diseases of the entire plant is increased.

In a preferred embodiment of the method, the aerial plant parts are treated with a formulation of the active ingredient I.

The publications cited at the outset describe synthesis routes for the preparation of the active ingredients used in the method according to the invention, the disclosure of which is hereby incorporated.

Especially preferred for the method according to the invention are active ingredients with the following meanings of the substituents, in each case alone or in combination, the disclosure of the publications cited being hereby incorporated:

Especially preferred for the method according to the invention are, as component 1, the active ingredients of the formulae II to VIII, in which V is $OCH_3$ and $NHCH_3$, Y is CH and N and T and Z independently of one another are CH and N.

Preferred active ingredients of the formula I in which Q is $N(—OCH_3)—COOCH_3$ are the compounds described in the publications WO 93/15046 and WO 96/01256.

Preferred active ingredients of the formula I in which Q is $C(═CH—OCH_3)—COOCH_3$ are the compounds described in the publications EP-A 178 826 and EP-A 278 595.

Preferred active ingredients of the formula I in which Q is $C(═N—OCH_3)—COOCH_3$ are the compounds described in the publications EP-A 253 213 and EP-A 254 426.

Preferred active ingredients of the formula I in which Q is $C(═N—OCH_3)—CONHCH_3$ are the compounds described in the publications EP-A 398 692, EP-A 477 631 and EP-A 628 540.

Preferred active ingredients of the formula I in which Q is $C(═CH—CH_3)—COOCH_3$ are the compounds described in the publications EP-A 280 185 and EP-A 350 691.

Preferred active ingredients of the formula I in which Q is $—CH_2O—N═C(R^1)—B$ are the compounds described in the publications EP-A 460 575 and EP-A 463 488.

Preferred active ingredients of the formula I in which A is —O—B are the compounds described in the publications EP-A 382 375 and EP-A 398 692.

Preferred active ingredients of the formula I in which A is $—CH_2O—N═C(R^1)—C(R^2)═N—OR^3$ are the compounds described in the publications WO 95/18789, WO 95/21153, WO 95/21154, WO 97/05103 and WO 97/06133.

Especially preferred are the active ingredients of the formula I in which

Q is $N(—OCH_3)—COOCH_3$,

A is $CH_2—O—$ and

B is 3-pyrazolyl or 1,2,4-triazolyl, where B has attached to it one or two substituents selected from the group of halogen, methyl and trifluoromethyl and phenyl and pyridyl, in particular 2-pyridyl, substituted by 1 to 3 radicals $R^b$.

These active ingredients are described by formula II,

II

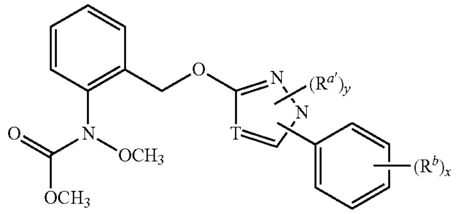

in which T is a carbon or a nitrogen atom, $R^{a'}$ is halogen, methyl and trifluoromethyl, y is zero, 1 or 2, $R^b$ is as defined for formula I, x is zero, 1, 2, 3 or 4.

More preferred active ingredients are those of formula II':

II'

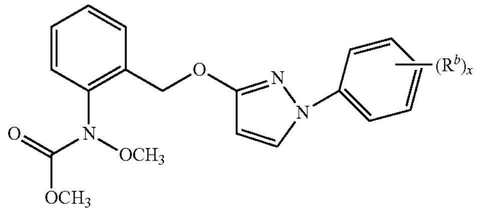

in which $R^b$ is as defined for formula I.

With regard to their use, the compounds compiled in the tables, which follow, are especially preferred.

TABLE I

II

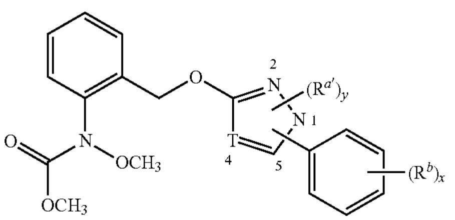

| No. | T | $(R^{a'})_y$ | Position of the group phenyl-$(R^b)_x$ | $(R^b)_x$ | Reference |
|---|---|---|---|---|---|
| I-1 | N | — | 1 | 2,4-$Cl_2$ | WO 96/01256 |
| I-2 | N | — | 1 | 4-Cl | WO 96/01256 |
| I-3 | CH | — | 1 | 2-Cl | WO 96/01256 |
| I-4 | CH | — | 1 | 3-Cl | WO 96/01256 |
| I-5 | CH | — | 1 | 4-Cl | WO 96/01256 |
| I-6 | CH | — | 1 | 4-$CH_3$ | WO 96/01256 |
| I-7 | CH | — | 1 | H | WO 96/01256 |
| I-8 | CH | — | 1 | 3-$CH_3$ | WO 96/01256 |
| I-9 | CH | 5-$CH_3$ | 1 | 3-$CF_3$ | WO 96/01256 |
| I-10 | CH | 1-$CH_3$ | 5 | 3-$CF_3$ | WO 99/33812 |
| I-11 | CH | 1-$CH_3$ | 5 | 4-Cl | WO 99/33812 |
| I-12 | CH | 1-$CH_3$ | 5 | — | WO 99/33812 |

TABLE II

III

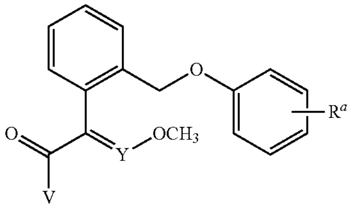

| No. | V | Y | $R^a$ | Reference |
|---|---|---|---|---|
| II-1 | $OCH_3$ | N | 2-$CH_3$ | EP-A 253 213 |
| II-2 | $OCH_3$ | N | 2,5-$(CH_3)_2$ | EP-A 253 213 |
| II-3 | $NHCH_3$ | N | 2,5-$(CH_3)_2$ | EP-A 477 631 |
| II-4 | $NHCH_3$ | N | 2-Cl | EP-A 398 692 |
| II-5 | $NHCH_3$ | N | 2-$CH_3$ | EP-A 398 692 |
| II-6 | $NHCH_3$ | N | 2-$CH_3$, 4-$OCF_3$ | EP-A 628 540 |
| II-7 | $NHCH_3$ | N | 2-Cl, 4-$OCF_3$ | EP-A 628 540 |
| II-8 | $NHCH_3$ | N | 2-$CH_3$, 4-$OCH(CH_3)$—$C(CH_3)$═$NOCH_3$ | EP-A 11 18 609 |
| II-9 | $NHCH_3$ | N | 2-Cl, 4-$OCH(CH_3)$—$C(CH_3)$═$NOCH_3$ | EP-A 11 18 609 |
| II-10 | $NHCH_3$ | N | 2-$CH_3$, 4-$OCH(CH_3)$—$C(CH_2CH_3)$═$NOCH_3$ | EP-A 11 18 609 |
| II-11 | $OCH_3$ | CH | 2,5-$(CH_3)_2$ | EP-A 226 917 |

TABLE III

IV

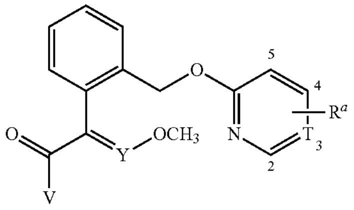

| No. | V | Y | T | $R^a$ | Reference |
|---|---|---|---|---|---|
| III-1 | $OCH_3$ | CH | N | 2-$OCH_3$, 4-$CF_3$ | WO 96/16047 |
| III-2 | $OCH_3$ | CH | N | 2-$OCH(CH_3)_2$, 4-$CF_3$ | WO 96/16047 |
| III-3 | $OCH_3$ | CH | CH | 2-$CF_3$ | EP-A 278 595 |
| III-4 | $OCH_3$ | CH | CH | 4-$CF_3$ | EP-A 278 595 |
| III-5 | $NHCH_3$ | N | CH | 2-Cl | EP-A 398 692 |
| III-6 | $NHCH_3$ | N | CH | 2-$CF_3$ | EP-A 398 692 |
| III-7 | $NHCH_3$ | N | CH | 2-$CF_3$, 4-Cl | EP-A 398 692 |
| III-8 | $NHCH_3$ | N | CH | 2-Cl, 4-$CF_3$ | EP-A 398 692 |

TABLE IV

V

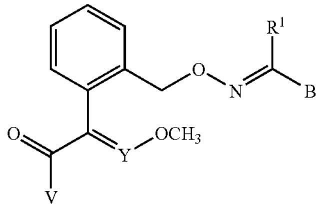

| No. | V | Y | $R^1$ | B | Reference |
|---|---|---|---|---|---|
| IV-1 | $OCH_3$ | CH | $CH_3$ | $(3-CF_3)C_6H_4$ | EP-A 370 629 |
| IV-2 | $OCH_3$ | CH | $CH_3$ | $(3,5-Cl_2)C_6H_3$ | EP-A 370 629 |
| IV-3 | $NHCH_3$ | N | $CH_3$ | $(3-CF_3)C_6H_4$ | WO 92/13830 |
| IV-4 | $NHCH_3$ | N | $CH_3$ | $(3-OCF_3)C_6H_4$ | WO 92/13830 |
| IV-5 | $OCH_3$ | N | $CH_3$ | $(3-OCF_3)C_6H_4$ | EP-A 460 575 |
| IV-6 | $OCH_3$ | N | $CH_3$ | $(3-CF_3)C_6H_4$ | EP-A 460 575 |
| IV-7 | $OCH_3$ | N | $CH_3$ | $(3,4-Cl_2)C_6H_3$ | EP-A 460 575 |
| IV-8 | $OCH_3$ | N | $CH_3$ | $(3,5-Cl_2)C_6H_3$ | EP-A 463 488 |
| IV-9 | $OCH_3$ | CH | $CH_3$ | CH═CH-$(4-Cl)C_6H_4$ | EP-A 936 213 |

TABLE V

VI

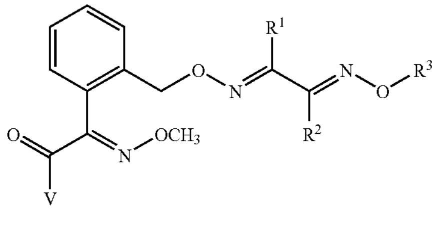

| No. | V | $R^1$ | $R^2$ | $R^3$ | Reference |
|---|---|---|---|---|---|
| V-1 | $OCH_3$ | $CH_3$ | $CH_3$ | $CH_3$ | WO 95/18789 |
| V-2 | $OCH_3$ | $CH_3$ | $CH(CH_3)_2$ | $CH_3$ | WO 95/18789 |
| V-3 | $OCH_3$ | $CH_3$ | $CH_2CH_3$ | $CH_3$ | WO 95/18789 |
| V-4 | $NHCH_3$ | $CH_3$ | $CH_3$ | $CH_3$ | WO 95/18789 |
| V-5 | $NHCH_3$ | $CH_3$ | 4-F-$C_6H_4$ | $CH_3$ | WO 95/18789 |
| V-6 | $NHCH_3$ | $CH_3$ | 4-Cl-$C_6H_4$ | $CH_3$ | WO 95/18789 |
| V-7 | $NHCH_3$ | $CH_3$ | 2,4-$C_6H_3$ | $CH_3$ | WO 95/18789 |
| V-8 | $NHCH_3$ | Cl | 4-F-$C_6H_4$ | $CH_3$ | WO 98/38857 |
| V-9 | $NHCH_3$ | Cl | 4-Cl-$C_6H_4$ | $CH_2CH_3$ | WO 98/38857 |
| V-10 | $NHCH_3$ | $CH_3$ | $CH_2C(═CH_2)CH_3$ | $CH_3$ | WO 97/05103 |
| V-11 | $NHCH_3$ | $CH_3$ | CH═$C(CH_3)_2$ | $CH_3$ | WO 97/05103 |

TABLE V-continued

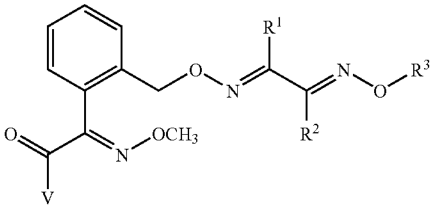

VI

| No. | V | $R^1$ | $R^2$ | $R^3$ | Reference |
|---|---|---|---|---|---|
| V-12 | $NHCH_3$ | $CH_3$ | $CH{=}C(CH_3)_2$ | $CH_2CH_3$ | WO 97/05103 |
| V-13 | $NHCH_3$ | $CH_3$ | $CH{=}C(CH_3)CH_2CH_3$ | $CH_3$ | WO 97/05103 |
| V-14 | $NHCH_3$ | $CH_3$ | $O—CH(CH_3)_2$ | $CH_3$ | WO 97/06133 |
| V-15 | $NHCH_3$ | $CH_3$ | $O—CH_2CH(CH_3)_2$ | $CH_3$ | WO 97/06133 |
| V-16 | $NHCH_3$ | $CH_3$ | $C(CH_3){=}NOCH_3$ | $CH_3$ | WO 97/15552 |

TABLE VI

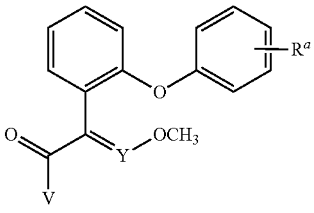

VII

| No. | V | Y | $R^a$ | Reference |
|---|---|---|---|---|
| VI-1 | $NHCH_3$ | N | H | EP-A 398 692 |
| VI-2 | $NHCH_3$ | N | $3\text{-}CH_3$ | EP-A 398 692 |
| VI-3 | $NHCH_3$ | N | $2\text{-}NO_2$ | EP-A 398 692 |
| VI-4 | $NHCH_3$ | N | $4\text{-}NO_2$ | EP-A 398 692 |
| VI-5 | $NHCH_3$ | N | 4-Cl | EP-A 398 692 |
| VI-6 | $NHCH_3$ | N | 4-Br | EP-A 398 692 |

TABLE VII

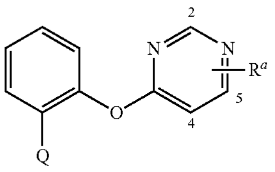

VIII

| No. | Q | $R^a$ | Reference |
|---|---|---|---|
| VII-1 | $C({=}CH—OCH_3)COOCH_3$ | $5\text{-}O\text{-}(2\text{-}CN—C_6H_4)$ | EP-A 382 375 |
| VII-2 | $C({=}CH—OCH_3)COOCH_3$ | $5\text{-}O\text{-}(2\text{-}Cl—C_6H_4)$ | EP-A 382 375 |
| VII-3 | $C({=}CH—OCH_3)COOCH_3$ | $5\text{-}O\text{-}(2\text{-}CH_3—C_6H_4)$ | EP-A 382 375 |
| VII-4 | $C({=}N—OCH_3)CONHCH_3$ | $5\text{-}O\text{-}(2\text{-}Cl—C_6H_4)$ | GB-A 2253624 |
| VII-5 | $C({=}N—OCH_3)CONHCH_3$ | $5\text{-}O\text{-}(2,4\text{-}Cl_2—C_6H_3)$ | GB-A 2253624 |
| VII-6 | $C({=}N—OCH_3)CONHCH_{33}$ | $5\text{-}O\text{-}(2\text{-}CH_3—C_6H_4)$ | GB-A 2253624 |
| VII-7 | $C({=}N—OCH_3)CONHCH_3$ | $5\text{-}O\text{-}(2\text{-}CH_3,3\text{-}Cl—C_6H_3)$ | GB-A 2253624 |
| VII-8 | $C({=}N—OCH_3)CONHCH_3$ | $4\text{-}F, 5\text{-}O\text{-}(2\text{-}CH_3—C_6H_4)$ | WO 98/21189 |
| VII-9 | $C({=}N—OCH_3)CONHCH_3$ | $4\text{-}F, 5\text{-}O\text{-}(2\text{-}Cl—C_6H_4)$ | WO 98/21189 |
| VII-10 | $C({=}N—OCH_3)CONHCH_3$ | $4\text{-}F, 5\text{-}O\text{-}(2\text{-}CH_3,3\text{-}Cl—C_6H_3)$ | WO 98/21189 |
| VII-11 | Q1 | $4\text{-}F, 5\text{-}O\text{-}(2\text{-}Cl—C_6H_4)$ | WO 97/27189 |
| VII-12 | Q1 | $4\text{-}F, 5\text{-}O\text{-}(2\text{-}CH_3,3\text{-}Cl—C_6H_3)$ | WO 97/27189 |
| VII-13 | Q1 | $4\text{-}F, 5\text{-}O\text{-}(2,4\text{-}Cl_2—C_6H_3)$ | WO 97/27189 |

Especially preferred are, in particular, the active ingredients: Compound I-5 (pyraclostrobin), II-1 (kresoxim-methyl), II-3 (dimoxystrobin), II-11 (ZJ 0712), III-3 (picoxystrobin), IV-6 (trifloxystrobin), IV-9 (enestroburin), V-16 (orysastrobin). VI-1 (metominostrobin), VII-1 (azoxystrobin), and VII-11 (fluoxastrobin).

The compounds I increase the tolerance of plants to viruses. They are especially important for controlling viruses on diverse crop plants such as tobacco, barley, cucumber, potatoes and beet, and on the seeds of these plants.

The inventive method is useful to induce tolerance in plants against viruses of various families, such as Avsunviroidae, Bromoviridae, Closteroviridae, Fosxivinda, Geminiviridae, Luteoviridae, Nanoviridae, Parititiviridae, Pospiviroidae, Potyviridae, Reoviridae, dae, Mononegavirales, Rhabdoviridae, Sequiviridae, Tombusviridae, and Tymoviridae.

It is particularly suitable to control the following genus: *Benyvirus, Ilarvirus, Cucumovirus, Oleavirus, Tospovirus, Caulimovirus, Soymovirus, Cavemovirus, Peluvirus, Closterovirus, Comovirus; Crinivirus, Ampelovirus, Fabavirus, Nepovirus, Allexivirus, Manadrivirus, Carlavirus, Capillovirus, Foveavirus, Potexvirus, Trichovirus, Vitivirus, Furovirus, Mastrevirus, Curtovirus, Begomovirus, Hordeivirus, Idaeovirus, Luteovirus, Polervirus, Eanmovirus, Nanovirus, Ophiovirus, Ourmiavirus, Alphacryptovirus, Betacryptovirus, Pecluvirus, Pomovirus, Potyvirus, Rymovirus Bymovirus, Macluravirus, Ipomovirus, Tritimovirus, Fijivirus, Phytoreovirus, Oryzavirus, Cytorhabdovirus, Nucleorhabdovirus. Sequivirus, Waikavirus, Sobemovirus, Tenuivirus, Tobamovirus, Tobravirus, Tombusvirus, Carmovirus, Necrovirus, Dianthovirus, Machlomovirus, Avenavirus, Tymovirus, Marafivirus, Maculavirus, Umbravirus, Varicosavirus, Pospiviroid, Hostuviroid, Cocadviroid, Apscaviroid, Coleviroid, Avsuniviroid*, and *Pelamoviroid.*

More particularly, the inventive method is useful for controlling the following species: Tobacco streak virus, Cucumber mosaic virus, Tomato spotted wilt virus, Soybean chlorotic mottle virus, Broad bean wilt virus 1, Tobacco ringspot virus, Potato virus X, Soil-borne wheat mosaic virus, Barley stripe mosaic virus, Potato leafroll virus, Ourmia melon virus, Peanut clump virus, Potato mop-top virus, Potato virus Y, Barley yellow mosaic virus, Wheat streak mosaic virus, Potato yellow dwarf virus, Tobacco necrosis virus satellite, Southern bean mosaic virus, Tobacco mosaic virus, Tobacco rattle virus, Tomato bushy stunt virus, Tobacco necrosis virus A, Maize chlorotic mottle virus, Maize rayado fino virus, and Potato spindle tuber viroid.

Specifically, they are suitable for controlling the following plant diseases:

- in tobacco, the tobacco mosaic virus and the tobacco necrosis virus,
- in beans, the bean common mosaic virus and the bean yellow mosaic virus,
- in barley, the barley stripe mosaic virus and the barley yellow dwarf virus (DYDV),
- in cucumbers, the cucumber green mottle mosaic virus and the cucumber mosaic virus,
- in potatoes, the potato X virus and the potato y virus,
- in beet, *rhizomnania* and beet mild yellowing virus.

The application of the compound I preferably is made during the first six weeks, preferably four weeks of the growth period of the plants, long before first protective application against fungi usually is made. Preferably repeated applications of the compound I are made.

The plant is treated before infection takes place, preferably several weeks to one week before the expected virus attack. During such timeframe one to 10 applications are carried out. A markedly reduced susceptibility of the plant to viral diseases is observed.

In case of vegetables and field crops the active ingredients are preferably applied shortly after germination of the plants, especially within the first four weeks after germination. In case of fruits and other perennial plants the first application is made before begin or within the first four weeks of the growth period. In all cases best efficacy is observed, when the application is repeated every 10 to 20 days.

The method according to the invention is preferably carried out as foliar application when applied to fruit and vegetables, such as potatoes, tomatoes, cucurbits, preferably cucumbers, melons, watermelons, garlic, onions, and lettuce. Preferably more than two applications, and up to 10 applications during a season are carried out.

The method according to the invention is preferably carried out as foliar application when applied to fruits, such as apples, stone fruits, and citrus. Preferably more than two applications, and up to 5 applications during a season are carried out.

The method of the invention can also be applied to field crops, such as soybeans, corn, cotton, tobacco, common beans, wheat, barley, peas, and others. In relation to these crops the method is preferably applied by treating the seeds or the plants. The plants are preferably treated with two to three applications.

For use in crop protection, the application rates are between 0.01 and 2.0 kg, preferably up to 1.0 kg of active ingredient per hectare, depending on the type of pathogen and the plant species.

In the treatment of seed, amounts of from 0.001 to 0.1 g, preferably 0.01 to 0.05 g, of active ingredient are generally required per kilogram of seed.

The compounds I can be converted into the formulations conventionally used for fungicides, for example solutions, emulsions, suspensions, dusts, powders, pastes and granules. The use form depends on the particular purpose; in any case, it should ensure fine and uniform distribution of the compound according to the invention.

Best results are obtained when a formulation is used which supports the transport of the active compounds into the plants, and the distribution within the entire plant in the sap.

The formulations are prepared in a known manner (see e.g. for review U.S. Pat. No. 3,060,084. EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsufonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxy-ethylene octylphenol ether, ethoxylated isooctylphenol, octylphenol, nonylphenol, alkyl-phenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfate waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophenyl and enzylalkoholhemiformal.

Seed Treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compounds I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound may also be used successfully in the ultra-low-volume process (ULV), it being possible to apply formulations comprising over 95% by weight of active compound, or even to apply the active compound without additives.

The following are examples of formulations: 1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

2. Products to be applied undiluted for foliar applications. For seed treatment purposes, such products may be applied to the seed diluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulation can be applied to the seed diluted or undiluted. Application to the seeds is carried out before sowing, either directly on the seeds.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

The note mentioning the effect of the active ingredients I in inducing resistance to viruses may be present as a label on the packaging or in product data sheets. The note may also be present in the case of preparations which can be used in combination with the active ingredients I.

The induction of resistance may also constitute an indication which may be the subject of official approval of the active ingredients I.

The action of the compounds of the general formula I was demonstrated by the following experiments:

Use examples for induction of resistance to viruses

Plant Material

For the experiments, tobacco plants (*Nicotinia tabacum* cv. *Xanthi-nc*) were grown at 25° C., an atmospheric humidity of 59% and a daily photoperiod of 16 hours (150-200 μM quanta/$s^{-1}$/$m^{-2}$) for 4 to 5 weeks in potting compost (standard soil type ED 73). Some of the plants were fed once per week by adding a commercial house-plant fertilizer (10% total nitrogen, 9% phosphate, 7% potash) to the irrigation water at the recommended rate.

Application of the Active Ingredient

The formulated active ingredient used took the form of water-dispersible granules with an active ingredient content of 20%. The concentrations used in the experiments (0.01-10 mM) are based on the active ingredient content. To prevent distribution of the active ingredient in the entire plant, the stalks of plants where a leaf had been infiltrated were removed above the treated leaf, using a sterile surgical blade.

After the application of the active ingredient, and also after infection with the virus at a later time, the plants were left to stand in the growth cabinet.

Virus infection and resistance assessment (following Malamy et al., SCIENCE Vol. 250, pp. 1002-1004 (1990)):

The various pretreated tobacco plants were infected with tobacco mosaic virus (TMV, strain U1). To this end, a viral stock solution was diluted with 50 mM phosphate buffer (pH 7) to a final concentration of 1 μg TMV coat protein/ml. Infection was carried out by gently rubbing leaves, whose surfaces had previously been sprinkled with silicon carbide, with a gauze bandage soaked in the TMV solution. Post-infection, the silicon carbide was rinsed from the leaves with a gentle water jet and the plants were left to stand under the above-described conditions. Infection with TMV was carried out 1 day after the pretreatment. Five to 7 days post-infection, the diameter of 10 to 20 lesions on the leaves was determined.

The lesion diameter is a measure of the acquired resistance of the plants, the smallest lesions representing the highest acquired resistance.

USE EXAMPLE 1

Individual leaves of the plants were perforated at several sites with a cannula, and the aqueous active ingredient solution was injected into the leaf at the perforation sites using a syringe (rate of application 2 to 5 ml/leaf). The insoluble components of the solution of the active ingredient had previously been removed either by sedimentation or by brief spinning (3 minutes at 5,000 g). In case of the control plants, the leaves were injected with water.

After 7 days, the diameter of the lesions on the leaves caused by TMV was determined in millimeters [mm].

In this test, the plants treated with 1 mM of the active ingredient I-5 in Table I showed lesions averaging 2.35 mm and the plants treated with 2.5 mM showed 1.8 mm, while the plants treated with pure water as control showed lesions of 3.55 mm.

USE EXAMPLE 2

One half of the treated leaf was infiltrated with the active ingredient solution (preparation as in Example 1), while the other half was infiltrated with water. This procedure was intended to exclude variations in the response between different leaves and to make possible a direct determination on the effect of the active ingredient.

After 5 days, the diameter of the lesions on the leaves caused by TMV was determined in millimeters [mm].

In this test the leaf zones treated with 0.5 and 1 mM of the active ingredient I-5 in Table I showed lesions averaging 2.75 and 2.85 mm, respectively, and the untreated leaf zones showed lesions of 4.15 and 4.25 mm, while the plants treated with pure water as control showed lesions of 3.2 and 3.35 mm.

USE EXAMPLE 3

Leaf halves of approx. 5-weeks-old tobacco plants (cultivar *Xanthi-nc*) were infiltrated with 1 mM active ingredient solution in 1% aqueous ethanol; the leaf halves of the controls were infiltrated with 1% aqueous ethanol.

Infection with TMV was carried our 1 day after treatment; the plants were evaluated after further 5 days. The data shown are the averages of the leaf areas which had died owing to viral attack (lesions) at the infection site on leaf halves treated with active ingredient or untreated leaf halves (controls):

Area of the lesions in comparison with the control:

| Active ingredient | Area in percent |
|---|---|
| I-5 | 53.0 |
| II-3 | 68.1 |
| III-4 | 60.3 |
| IV-3 | 76.1 |
| V-16 | 63.8 |
| VII-1 | 62.1 |

USE EXAMPLE 4

The procedure of use example 3 was followed, but infection was carried out 2 days after the treatment and the plants were evaluated after further 5 days.

Area of the lesions in comparison with the control:

| Active Ingredient | Area In percent |
|---|---|
| II-3 | 62.7 |
| III-4 | 78.4 |
| VII-1 | 70.4 |

USE EXAMPLE 5

Spraying the Leaves with Active Ingredient Solutions

In each case 2 mM active ingredient were dissolved in water with the aid of a universal wetter in the ratio 1:1 (w/w) and sprayed onto the leaf halves of 5-week-old tobacco plants (cultivar *Xanthi-nc*) (leaf halves of the controls were sprayed with dissolved wetter only).

Infection with TMV was carried out 5 days after the treatment, and the plants were evaluated after further 4 days. The data shown are the averages of the leaf areas which had died owing to viral attack (lesions) at the infection site on leaf halves treated with active ingredient or untreated leaf halves (controls):

Area of the lesions in comparison with the control:

| Active ingredient | Area in percent |
|---|---|
| II-3 | 49.6 |
| III-4 | 73.6 |
| VII-1 | 68.3 |

USE EXAMPLE 6

Enhanced Plant Growth and Tolerance to Viral Infection Following Treatments

The experiments were performed in greenhouse of under appropriate growing conditions for tomatoes. Tomato plants (cultivar Gaucho) were grown in pots until development of the first two true leaves. Then the plantlets were sprayed with different concentrations of formulated Pyraclostrobin (compound I-5; commercial fungicide Cabrio Top® of BASF Aktiengesellschaft). These treatments were done either 120 hours before or following inoculation of the plantlets with TMV, representing protective and curative situation. The treatments were run with 5 replicates, each containing 3 plantlets. 30 days after last treatment the plants were analyzed for visual plant growth (altitude and dry mass) and chlorophyll content (photometric measurement of extracts). Also the virus titre was determined (ELISA).

| No. | Treatment | Chlorophyll [μg fresh weight] | Dry weight [g] | Altidude [cm] |
|---|---|---|---|---|
| 1 | Non infected control | 12.5 bc | 1.54 a | 25.59 a |
| 2 | TMV infected, untreated | 10.8 bc | 0.30 ef | 9.53 f |
| 3 | Cabrio Top 1.5 $g/L^{-1}$ Preventive | 18.6 a | 0.74 b | 18.3B bc |
| 4 | Cabrio Top 1.5 $g/L^{-1}$ Curative | 11.5 bc | 0.35 ef | 12.48 def |

Same letters indicate non significant differences (Tukey; $P \leqq 0.05$).

As shown by the data, protective treatment of plants with Pyraclostrobin can prevent growth inhibition and loss of leaf chlorophyll caused by TMV infection. Curative treatment showed no advantage compared with untreated plants.

The invention claimed is:

1. A method of inducing virus tolerance of plants which comprises treating the plants, the soil or seeds, repeatedly during the first six weeks of the growth period of the plant, with an effective amount of a compound of the formula I

I

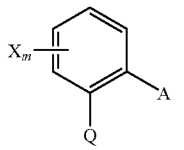

in which

X is halogen, $C_1$-$C_4$-alkyl or trifluoromethyl;

m is 0 or 1;

Q is $C(=CH-CH_3)-COOCH_3$, $C(=CH-OCH_3)-COOCH_3$, $C(=N-OCH_3)-CONHCH_3$, $C(=N-OCH_3)-COOCH_3$, $N(-OCH_3)-COOCH_3$, or a group Q1

Q1

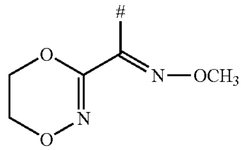

A is $-O-B$, $-CH_2O-B$, $-OCH_2-B$, $-CH_2S-B$, $-CH=CH-B$, $-C\equiv C-B$, $-CH_2O-N=C(R^1)-B$, $-CH_2S-N=C(R^1)-B$, $-CH_2O-N=C(R^1)-CH=CH-B$ or $-CH_2O-N=C(R^1)-C(R^2)=N-OR^3$, where B is phenyl, naphthyl, 5-membered or 6-membered hetaryl or 5-membered or 6-membered heterocyclyl, containing one to three N atoms and/or one O or S atom or one or two O and/or S atoms, the ring systems being unsubstituted or substituted by one to three radicals $R^a$:

$R^a$ is cyano, nitro, amino, aminocarbonyl, aminothiocarbonyl, halogen, $C_1$-$C_6$-alkyl, $C_1$-$C_6$-haloalkyl, $C_1$-$C_6$-alkylcarbonyl, $C_1$-$C_6$-alkylsulfonyl, $C_1$-$C_6$-alkylsulfinyl, $C_3$-$C_6$-cycloalkyl, $C_1$-$C_6$-alkoxy, $C_1$-$C_6$-haloalkoxy, $C_1$-$C_6$-alkyloxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylamino-carbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, phenyl, phenoxy, benzyl, benzyloxy, 5- or 6-membered heterocyclyl, 5- or 6-membered hetaryl, 5- or 6-membered hetaryloxy, C(=NOR$^a$)—OR$^b$ or OC(R$^a$)$_2$—C(R$^b$)=NOR$^b$, the cyclic radicals, in turn, being unsubstituted or substituted by one to three radicals R$^b$:

R$^b$ is cyano, nitro, halogen, amino, amino-carbonyl, aminothio-carbonyl, $C_1$-$C_6$-alkyl, $C_1$-$C_6$-haloalkyl, $C_1$-$C_6$-alkylsulfonyl, $C_1$-$C_6$-alkylsulfinyl, $C_3$-$C_6$-cycloalkyl, $C_1$-$C_6$-alkoxy, $C_1$-$C_6$-haloalkoxy, $C_1$-$C_6$-alkoxy-carbonyl, $C_1$-$C_6$-alkylthio, $C_1$-$C_6$-alkylamino, di-$C_1$-$C_6$-alkylamino, $C_1$-$C_6$-alkylamino-carbonyl, di-$C_1$-$C_6$-alkylaminocarbonyl, $C_1$-$C_6$-alkylaminothiocarbonyl, di-$C_1$-$C_6$-alkyl-aminothiocarbonyl, $C_2$-$C_6$-alkenyl, $C_2$-$C_6$-alkenyloxy, $C_3$-$C_6$-cycloalkyl, $C_3$-$C_6$-cycloalkenyl, phenyl, phenoxy, phenylthio, benzyl, benzyloxy, 5- or 6-membered heterocyclyl, 5- or 6-membered hetaryl, 5- or 5-membered hetaryloxy or C(=NOR$^A$)—OR$^B$;

R$^A$, R$^B$ are hydrogen or $C_1$-$C_6$-alkyl;

R$^1$ is hydrogen, cyano, $C_1$-$C_4$-alkyl, $C_1$-$C_4$-haloalkyl, $C_3$-$C_6$-cycloalkyl, $C_1$-$C_4$-alkoxy;

R$^2$ is phenyl, phenylcarbonyl, phenylsulfonyl, 5- or 6-membered hetaryl, 5- or 6-membered hetarylcarbonyl or 5- or 6-membered hetarylsulfonyl, the ring systems being unsubstituted or substituted by one to three radicals R$^a$, $C_1$-$C_{10}$-alkyl, $C_3$-$C_6$-cycloalkyl, $C_2$-$C_{10}$-alkenyl, $C_2$-$C_{10}$-alkynyl, $C_1$-$C_{10}$-alkylcarbonyl, $C_2$-$C_{10}$-alkenyl-carbonyl, $C_3$-$C_{10}$-alkynylcarbonyl, $C_1$-$C_{10}$-alkyl-sulfonyl, or C(=NOR$^A$)—OR$^B$, the hydrocarbon radicals of these groups being unsubstituted or substituted by one to three radicals R$^c$:

R$^c$ is cyano, nitro, amino, aminocarbonyl, aminothiocarbonyl, halogen, $C_1$-$C_6$-alkyl, $C_1$-$C_6$-haloalkyl, $C_1$-$C_6$-alkylsulfonyl, $C_1$-$C_6$-alkylsulfinyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylamino-thiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkyloxy, 5- or 6-membered heterocyclyl, 5- or 6-membered heterocyclyloxy, benzyl, benzyloxy, phenyl, phenoxy, phenylthio, 5- or 6-membered hetaryl, 5- or 6-membered hetaryloxy and hetarylthio, it being possible for the cyclic groups, in turn, to be partially or fully halogenated or to have attached to them one to three radicals R$^a$; and R$^3$ is hydrogen, $C_1$-$C_6$-alkyl, $C_2$-$C_6$-alkenyl, $C_2$-$C_6$-alkynyl, the hydrocarbon radicals of these groups being unsubstituted or substituted by one to three radicals R$^c$;

which is taken up by the plants or seeds, during the first six weeks of the growth period of the plants, or germination of the seeds.

2. The method of claim 1, wherein in formula I the index m is zero and the substituents have the following meanings:

Q is C(=CH—$CH_3$)—$COOCH_3$, C(=CH—$OCH_3$)—$COOCH_3$, C(=N—$OCH_3$)—$CONHCH_3$, C(=N—$OCH_3$)—$COOCH_3$, or N(—$OCH_3$)—$COOCH_3$;

A is —O—B, —$CH_2$O—B, —O$CH_2$—B, —$CH_2$O—N=C(R$^1$)—B, or $CH_2$—O—N=C(R$^1$)—C(R$^2$)=N—OR$^3$;

B is phenyl, pyridyl, pyrimidinyl, pyrazolyl, triazolyl, these ring systems being substituted by one or two radicals R$^a$;

R$^1$ is hydrogen, cyano, $C_1$-$C_4$-alkyl, $C_1$-$C_4$-haloalkyl, $C_3$-$C_6$-cycloalkyl, or $C_1$-$C_4$-alkoxy;

R$^2$ is $C_1$-$C_6$-alkyl, $C_2$-$C_{10}$-alkenyl, $C_3$-$C_6$-cycloalkyl, these groups being unsubstituted or substituted by one or two radicals R$^{b'}$;

R$^{b'}$ is $C_1$-$C_6$-alkyl, $C_3$-$C_6$-cycloalkyl, $C_1$-$C_6$-alkoxy, $C_1$-$C_6$-haloalkoxy, benzyl, phenyl or phenoxy;

phenyl which is unsubstituted or substituted by one or two radicals R$^a$; and

R$^3$ is $C_1$-$C_6$-alkyl, $C_2$-$C_{10}$-alkenyl or $C_2$-$C_{10}$-alkynyl.

3. The method of claim 1, wherein the compound is formula II

II

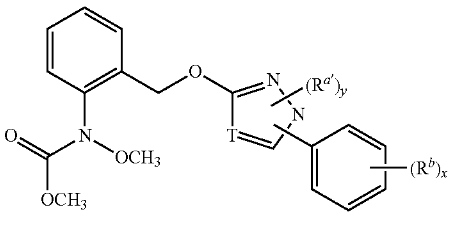

in which

T is a carbon or a nitrogen atom,

R$^{a'}$ is halogen, methyl and trifluoromethyl, y is zero, 1 or 2,

R$^b$ is as defined for formula I, x is zero, 1, 2, 3 or 4.

4. The method of claim 1, wherein the compound is formula III in which

III

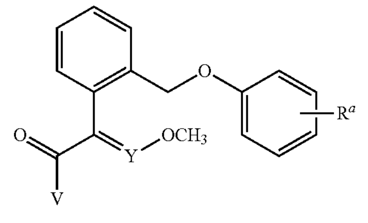

T is a carbon or a nitrogen atom,

R$^a$ represents one or two identical or different groups selected from halogen, $C_1$-$C_6$-alkyl, $C_1$-$C_6$-alkoxy, halogenmethyl, halogenmethoxy, methyl and trifluoromethyl, which R$^a$ groups are unsubstituted or substituted by a $C_1$-$C_6$-alkoxyimino group;

V is $OCH_3$, or $NHCH_3$; and

Y is CH or N.

5. The method of claim 1, wherein compound I is selected from: pyraclostrobin, kresoxim-methyl, dimoxystrobin, 2-(ortho((2,5-Dimethylphenyl-oxymethylene)phenyl)-3-methoxyacrylic acid methyl ester, picoxystrobin, trifloxstrobin, enestroburin, orysastrobin, metominostrobin, azoxystrobin, and fluoxastrobin.

6. The method of claim 1, wherein compound I is selected from: pyraclostrobin, kresoxim-methyl, dimoxystrobin, 2-(ortho-((2,6-Dimethylphenyl-oxymethylene)phenyl)-3-methoxyacrylic acid methyl ester, picoxystrobin, trifoxystrobin, enestroburin, orysastrobin, metominostrobin, azoxystrobin, and fluoxastrobin.

7. The method of claim 1, wherein compound I is selected from: azoxystrobin, pyraclostrobin, and picoxystrobin.

8. The method of claim 1 wherein application is made during the first four weeks of the growth period of the plants or germination of the seeds.

9. The method of claim 1 wherein repeated application of a compound I is made every 10 to 20 days.

10. The method of claim 1 wherein two to ten applications of a compound I during a season are made.

11. The method of claim 1 which is carried out as foliar application.

12. The method of claim 1 applied to vegetables and field crops wherein application is carried out shortly after germination of the plants.

13. The method of claim 12 wherein application is carried out within the first four weeks after germination.

14. The method of claim 1 which is applied to fruit and vegetables which comprises more than two, and up to ten applications of a compound I.

15. The method of claim 1 which is applied to fruits and other perennial plants wherein a first application is made before begin of the growth period.

16. The method of claim 15 wherein the first application is made within the first four weeks of the growth period.

17. The method of claim 10 which is applied to potatoes, tomatoes, cucurbits, cucumbers, melons, watermelons, garlic, onions, and lettuce.

18. The method of claim 10 which is applied to apples, stone fruits, or citrus.

19. The method of claim 10 which is applied to soybeans, corn, cotton, tobacco, common beans, wheat, barley, and peas.

20. The method of claim 1, wherein the method comprises treating the plants, the soil or seeds, with a treatment consisting of an effective amount of a single compound of the formula I.

21. The method of claim 7, wherein two to ten applications of the compound I are made during a season; and/or the treatment is carried out as foliar application; and/or the compound I is applied to a fruit or vegetable plant.

22. The method of claim 21, wherein the plant is selected from the group consisting of potatoes, tomatoes, cucurbits, cucumbers, melons, watermelons, garlic, onions, lettuce, apples, stone fruits, citrus, soybeans, corn, cotton, tobacco, common beans, wheat, barley, and peas.

* * * * *